(12) United States Patent
Haueter et al.

(10) Patent No.: US 8,500,700 B2
(45) Date of Patent: *Aug. 6, 2013

(54) DOSING UNIT, AMBULATORY INFUSION DEVICE COMPRISING DOSING UNIT AND METHOD FOR OPERATING A DOSING UNIT

(75) Inventors: Ulrich Haueter, Grosshoechstetten (CH); Martin Wyss, Burgdorf (CH); Florian Kuehni, Wabern (CH)

(73) Assignee: Roche Diagnostics International AG, Rotkreuz (CH)

( * ) Notice: Subject to any disclaimer, the term of this patent is extended or adjusted under 35 U.S.C. 154(b) by 52 days.

This patent is subject to a terminal disclaimer.

(21) Appl. No.: 13/046,022

(22) Filed: Mar. 11, 2011

(65) Prior Publication Data

US 2011/0224644 A1   Sep. 15, 2011

Related U.S. Application Data

(63) Continuation of application No. PCT/EP2009/005447, filed on Jul. 28, 2009.

(30) Foreign Application Priority Data

Sep. 12, 2008 (EP) .................................. 08016075

(51) Int. Cl.
*A61M 5/00* (2006.01)
(52) U.S. Cl.
USPC ........... 604/208; 604/152; 604/211; 604/248; 417/214; 92/140
(58) Field of Classification Search
USPC ................. 604/152, 187, 207, 208, 210, 211, 604/246, 248, 249; 91/36, 138, 140; 417/214; 92/36, 138
See application file for complete search history.

(56) References Cited

U.S. PATENT DOCUMENTS 3,631,654 A   1/1972  Riely et al.
5,045,096 A   9/1991  Quang et al.
(Continued)

FOREIGN PATENT DOCUMENTS

DE   3832028 A1   3/1990
EP   0980690 A2   2/2000
(Continued)

OTHER PUBLICATIONS

Search Report for International Application No. PCT/EP2009/005447 dated Dec. 2, 2009.

(Continued)

*Primary Examiner* — Kevin C Sirmons
*Assistant Examiner* — Emily Schmidt
(74) *Attorney, Agent, or Firm* — Dinsmore & Shohl LLP (57) ABSTRACT

A dosing unit for an ambulatory infusion device and a method of operation are disclosed. The dosing unit includes a stationary member, a movable member, and a plunger. The movable member and the stationary member, together, make a charging valve and a discharging valve. The plunger is located, at least in part, in a metering cavity of the movable member and the movable member is adapted to selectively couple and decouple a driving unit, such that, by operating the driving unit with the movable member being coupled with the driving unit, the movable member moves with the plunger to maintain a position of the plunger relative to the movable member along a displacement axis, and by operating the driving unit with the movable member being decoupled from the driving unit, the plunger is displaced while the position of the movable member is maintained.

16 Claims, 4 Drawing Sheets

U.S. PATENT DOCUMENTS

| | | | |
|---|---|---|---|
| 5,807,321 | A | 9/1998 | Stoker et al. |
| 6,568,923 | B2 * | 5/2003 | Ikuta ............................ 417/462 |
| 2001/0025189 | A1 | 9/2001 | Haueter et al. |
| 2005/0033148 | A1 | 2/2005 | Haueter et al. |
| 2010/0049127 | A1 | 2/2010 | Haueter et al. |

FOREIGN PATENT DOCUMENTS

| | | |
|---|---|---|
| EP | 1486218 A2 | 12/2004 |
| EP | 1754505 A1 | 2/2007 |
| EP | 1970677 A1 | 9/2008 |
| WO | 9320864 A1 | 10/1993 |
| WO | 2006056828 A1 | 6/2006 |
| WO | WO2007/000064 A1 | 4/2007 |
| WO | 2007119149 A2 | 10/2007 |
| WO | 2007141681 A2 | 12/2007 |
| WO | 2008110263 A1 | 9/2008 |

OTHER PUBLICATIONS

European Search Report for Application No. 08016075.7-2320 dated Feb. 23, 2009.

European Application No. 11004169.6 Search Report dated Jul. 27, 2011.

* cited by examiner

DOSING UNIT, AMBULATORY INFUSION DEVICE COMPRISING DOSING UNIT AND METHOD FOR OPERATING A DOSING UNIT

CROSS REFERENCE TO RELATED APPLICATIONS

This application is a continuation of International Application No. PCT/EP2009/005447 filed Jul. 28, 2009, which claims priority to European Application 08016075.7 filed Sep. 12, 2008.

TECHNICAL FIELD

The present disclosure is related to dosing units for ambulatory infusion devices and to ambulatory infusion devices comprising such dosing units.

BACKGROUND

Ambulatory infusion devices are known, for example, in the therapy of Diabetes Mellitus by Continuous Subcutaneous Insulin Infusion (CSII), as well as in pain therapy or cancer therapy. Those ambulatory infusion pumps are manufactured, among others, by Disetronic Medical Systems AG, Switzerland, and are available, e.g., under the name ACCU-CHEK® Spirit for CSII therapy.

The above-referenced ambulatory infusion devices are typically a syringe driver type. A number of drawbacks of such syringe driver type devices are known in the art. In particular, these devices have limited precision because they meter very small drug amounts, typically in the nano-liter range, out of a drug cartridge having an overall drug volume in the milliliter range. Therefore, additional concepts and architectures have been proposed that use a dedicated dosing unit downstream from the drug reservoir. These concepts include a micro membrane pump or a micro piston pump that are coupled to a drug reservoir and designed for precise metering of small volumes. While several designs for such dosing units are known in the art, they are complex, expensive and difficult to manufacture at a large scale because they integrate a number of components, including metering components and valves, and are frequently made from materials that are costly and/or difficult to manufacture, such as silicon. Accordingly, improved dosing units and ambulatory infusion devices comprising dosing units are required.

SUMMARY

In one embodiment, a dosing unit for an ambulatory infusion device includes a stationary member, a movable member, and a plunger. The movable member and the stationary member, in combination, make a charging valve and a discharging valve, where the charging valve is adapted to be in fluid communication with a drug reservoir and the discharging valve is adapted to be in fluid communication with an outlet assembly. The movable member is movable between a charging valve position, in which the charging valve is open and the discharging valve is closed, and a discharging valve position, in which the discharging valve is open and the charging valve is closed. The plunger is located, at least in part, in a metering cavity of the movable member and is adapted to displace in the metering cavity along a displacement axis between a distal plunger end position and a proximal plunger end position. The plunger is adapted to couple continuously to a driving unit and the movable member is adapted to selectively couple and decouple to the driving unit such that, by operating the driving unit with the movable member being coupled with the driving unit, the movable member moves with the plunger as to maintain a position of the plunger relative to the movable member along the displacement axis, and that, by operating the driving unit with the movable member being decoupled from the driving unit, the plunger is displaced while a position of the movable member is maintained.

In another embodiment, a method for operating a metering unit for an ambulatory infusion device includes providing a dosing unit and a driving unit, coupling a plunger of the dosing unit, the plunger being located, at least in part, in a metering cavity of a movable member of the metering unit and being adapted for displacement in the metering cavity along a displacement axis. The method also includes coupling the movable member of the dosing unit to the driving unit with the plunger being further coupled to the driving unit, moving the movable member into a charging valve position with a position of the plunger relative to the movable member along the displacement axis being maintained. The method further includes decoupling the movable member from the driving unit with the plunger being further coupled to the driving unit, displacing the plunger along the displacement axis in a distal direction with the position of the movable member being maintained, thus charging the metering cavity, coupling the movable member of the dosing unit with the driving unit, with the plunger being further coupled to the driving unit, and moving the movable member into a discharging valve position, with the position of the plunger relative to the movable member along the displacement axis being maintained. The method further includes decoupling the movable member from the driving unit with the plunger being further coupled to the driving unit, and displacing the plunger along the displacement axis in a proximal direction with the position of the movable member being maintained, thus discharging the metering cavity.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

BRIEF DESCRIPTION OF THE DRAWINGS

The following detailed description of specific embodiments of the present invention can be best understood when read in conjunction with the drawings enclosed herewith and in which.

The embodiments set forth in the drawings are illustrative in nature and not intended to be limited of the invention defined by the claims. Moreover, individual features of the drawings and invention will be more fully apparent and understood in view of the detailed description.

DETAILED DESCRIPTION

Embodiments of the present disclosure are directed to dosing units and ambulatory infusion devices comprising dosing units that are reliable and cost efficient in large scale manufacture, as well as methods for operating such dosing units. Some aspects of such dosing unit are disclosed by co-owned European patent application No. 07104240.2.

In one embodiment, the present disclosure is direct towards a dosing unit for an ambulatory infusion device, where the dosing unit includes:

a) a stationary member; and b) a movable member, where the movable member and the stationary member, in combination, make a charging valve and a discharging valve. The charging valve is adapted to be in fluid communication with a drug reservoir and the discharging valve is adapted to be in fluid communication with an outlet assembly. The movable member is movable between a charging valve position, in which the charging valve is open and the discharging valve is closed, and a discharging valve position, in which the discharging valve is open and the charging valve is closed. The dosing unit also includes:

c) a plunger located, at least in part, in a metering cavity of the movable member and adapted for displacement in the metering cavity along a displacement axis between a distal plunger end position and a proximal plunger end position, where the plunger is adapted to couple continuously to a driving unit and the movable member is adapted to selectively couple and decouple to the driving unit. By operating the driving unit with the movable member being coupled to the driving unit, the movable member moves with the plunger as to maintain a position of the plunger relative to the movable member along the displacement axis, and that, by operating the driving unit with the movable member being decoupled from the driving unit, the plunger is displaced while a position of the movable member is maintained.

The stationary member and the movable member may include a set of valve apertures such that a movable charging valve aperture is aligned with a stationary charging valve aperture if the charging valve is open and a movable discharging valve aperture is aligned with a stationary discharging valve aperture if the discharging valve is open. In some embodiments, the movable member includes a single movable valve aperture, which may serve as both the movable charging valve aperture and the movable discharging valve aperture depending on the position of the movable member.

In some embodiments, neither the charging valve nor the discharging valve is open if the movable member is in a position other than the charging valve position or the discharging valve position.

In some embodiments, the movable member and the stationary member contact each other around the valve apertures to form a fluid-tight seal. The sealing force resulting from this contact may be used to control operation of the metering unit in some embodiments, as will be described below. In some embodiments, the stationary member also serves as a bearing for the movable member.

The metering cavity includes a closed proximal front and an open distal front. The metering cavity may be limited by a front face, which is formed by the inner face of a proximal front wall of the movable member, and a circumferential face, which is formed by the inner face of a circumferential wall of the movable member. The at least one movable valve aperture may be located in close axial proximity to the proximal front or in the proximal front of the metering cavity. In the proximal plunger end position, a proximal plunger front may be close to the proximal front and/or contact the proximal front of the metering cavity. As used herein, the terms "proximal" and "distal" are discussed in reference to the proximal front. Accordingly, the proximal direction is the direction pointing away from the distal front along the displacement axis towards the proximal front, while the distal direction is the direction pointing away from the proximal front along the displacement axis towards the distal front. As used herein, the proximal plunger front is used as reference for the plunger position along the displacement axis. Alternatively, however, the charging valve and the discharging valve may be located at the distal end of the movable member, with certain modifications being required.

The proximal plunger front forms a movable limiting surface of a variable metering volume, where the other limiting surfaces of the metering volume are defined by the surfaces of the metering cavity. The metering volume is the fluid filled volume of the metering cavity. If the plunger is in the proximal plunger end position, the metering volume is minimal and/or approaches zero. If the plunger is in the distal plunger end position, the metering volume is maximal.

The section of the metering cavity in which the proximal plunger front may move, i.e., the section axially defined by the distal plunger end position and the proximal plunger end position, is referred to as the metering section. The axial distance between the distal plunger end position and the proximal plunger end position is referred to as the displacement distance.

The plunger may include a plug section, which is in fluid contact with its proximal front, where the proximal front of the plug section is the proximal plunger front. The circumference of the plug section and the inner face of the metering section, in combination, form a fluid tight seal. Alternatively to a plug section being part of the plunger, a plug may be coupled to the plunger. For clarity reasons, however, the proximal front of the plug is also referred to as the "proximal plunger front" if the plug is a dedicated element.

In some embodiments, the metering cavity is cylindrical, where the cylinder axis of the metering cavity is the displacement axis. The plunger and the movable member, in combination, form a syringe-like component. The outer shape of the movable member may, at least in part, be cylindrical, such that the movable member is a hollow cylinder closed at its proximal front by a proximal front wall and open at its distal front, and include a cylindrical circumferential wall.

For the usage in the framework of diabetes therapy by CSII, the dosing unit may be designed for a maximum metering volume in the range of 4 to 20 International Units. For some embodiments that include a cylindrical metering cavity, the ratio of the displacement distance of the plunger to the diameter of the metering cavity may be in a range of 1:1 to 10:1. However, other dimensions, as well as larger or smaller ratios are contemplated.

The dosing unit may be a disposable product that is used for administering the drug volume contained within one drug reservoir only. The components of the dosing unit are, at least in part, made from plastic and manufactured by standard injection molding techniques. The plug section of the plunger or a separate plug may be made from a rubber or plastic material and may include seal features such as O-ring seals that are in contact with the inner circumferential face of the metering cavity. In some embodiments, the plug section is integral with additional components of the plunger. In some embodiments, the plunger is made in one piece.

If the movable member is coupled to the driving unit, the movable member is coupled to the driving unit directly or via intermediate components. In some preferred embodiments, the movable member couples to the driving unit via the plunger, as described below in more detail.

The coupling of the movable member to the drive unit may be continuous for the time of the metering sequence of the dosing unit. The movable member may, however, be decoupled from the drive unit for a short time, e.g., for cleaning or checking purposes where required in some embodiments. The metering sequence time of a dosing unit is typically on the order of a few days for the metering sequence in insulin infusion devices. The lifetime of the drive unit may be much longer, for example 4 years and/or generally unlimited.

In some embodiments, the movable member and the plunger move synchronously, that is, without relative motion, when operating the driving unit to which the plunger is coupled.

As used herein, the term "couple" refers to an operative coupling including a coupling capable of force and/or torque transmission such that an element coupled to the driving unit may be moved by a force and/or torque received from the driving unit. The movable member is referred to as being "coupled" if it is coupled to the driving unit and is referred to as being "decoupled" if the movable member is decoupled from the driving unit.

Embodiments of dosing units according the present disclosure allow metering sequences to be performed in a cyclical manner, where a metering sequence is described by a charging subsequence and a discharging subsequence, where each subsequence includes a valve switching step and a plunger displacing step according to the following table:

| Sub Sequence | Step | Step Type | Description |
| --- | --- | --- | --- |
| Charging | (a) | valve switching | Moving the movable member into its charging valve position, thus closing the discharging valve followed by opening the charging valve |
| | (b) | plunger displacing | Displacing the plunger in the distal direction, thus drawing fluid via the charging valve out of a drug reservoir and into the metering cavity |
| Discharging | (c) | valve switching | Moving the movable member into its discharging valve position, thus closing the charging valve followed by opening the discharging valve. |
| | (d) | plunger displacing | Displacing the plunger in the proximal direction, thus forcing fluid via the discharging valve out of the metering cavity and into the outlet assembly. |

The movable member is coupled for the valve switching steps and is decoupled for the plunger displacing steps. Because the plunger maintains its position in the metering cavity along the displacement axis for the valve switching steps, while the movable member maintains its position for the plunger displacing steps, the valve switching steps and the plunger displacing steps are separated from each other such that no substantial errors result from moving the movable member. As described below in further detail, embodiments of the dosing units according to the present disclosure perform all steps of a metering sequence and control the transition between the steps using only one driving unit.

In some embodiments, the plunger may be positioned between the distal plunger end position and the proximal plunger end position in a uniform manner. Therefore, a dosing unit according to these embodiments allows the displacing steps to be interrupted and continued without influencing the state of the charging valve and the discharging valve; that is, without performing, fully or in part, either of the switching steps. Fluid may be drawn into the metering cavity and may be forced out of the metering cavity in many small steps, which are only limited by the resolution of the drive system. This may assist in administering very small drug amounts, such as required, for example, in diabetes therapy by CSII. Dimensions of a dosing unit used in CSII therapy are provided below.

In some embodiments, the coupling and decoupling of the movable member is controlled, at least in part, by controlling the driving direction of the driving unit of the infusion device. In some embodiments, coupling and decoupling of the movable member is controlled, at least in part, by controlling the driving direction and controlling the starting and the stopping of the driving unit. Embodiments that include these features are described below in more detail.

In some embodiments, the movable member is rotatable with respect to the stationary member between its charging valve position and its discharging valve position, where the axis of rotation is the displacement axis.

In some embodiments, the stationary member and the movable member are designed such that the movable member is limited to rotate only between its charging valve position and its discharging valve position. The corresponding angle of rotation may, for example, be 180°, but larger or smaller angles of rotation may be used as well. For this embodiment, the movable member is supported by a rotational bearing, which may be included in the stationary member, as well as also including the stationary valve apertures. Additionally, or alternatively to the stationary member, other bearings may be used for supporting the movable member. In the axial direction, the movable member may be held in a fixed position.

In some embodiments that include a rotatable movable member, the plunger includes an outside thread and the movable member comprises an inside thread. The threads enable the plunger to be displaced along the length of the metering cavity in a screw-like manner. In additional embodiments, the movable member includes an outside thread while the plunger includes an inside thread. The threads are designed for a threaded engagement without substantial play and/or backlash.

In the following, the terms "thread" and "threaded" generally refer to right-hand threads as commonly used. However, left-hand-threads may alternatively be employed with the required modifications. The flank profile may generally be a standard thread profile or may be especially optimized for play-free engagement and force and/or torque transmission, such as an Acme thread form.

The thread pitch may be selected based on such factors as maximum volume of the metering section, dimensions of the metering cavity and required metering resolution. In the framework of an ambulatory infusion device for CSII, the pitch may be in the range of 0.5 mm to 2 mm.

The outside thread and the inside thread transform a rotational driving motion into a screw-like translation motion of the plunger along the displacement axis in the metering cavity. The inside thread of the metering cavity may be elongated and extend over a threaded section of the metering cavity in a distal direction away from the metering section at a length corresponding to the displacement distance or longer.

For these embodiments, the plunger includes an elongated plunger shaft, where the plunger shaft projects in a distal direction from the plug section or the plunger. The length of the plunger shaft is determined by the plunger displacement distance. The plunger shaft includes the outside thread at its distal end. The length of the outside thread is shorter than the length of the inside thread, and may be as short as one winding or less.

An engagement without substantial play and/or backlash may be achieved by biasing the threaded engagement. Biasing may be achieved by using the axial and/or radial elasticity of the plunger shaft and/or the outside thread of the plunger. For the purpose of biasing, the plunger shaft may include or be made of one or more radially elastic legs, the legs carrying the outside thread at their distal end. Elastic deformation of the at least one leg creates a biasing force that is exerted by the outside thread onto the inside thread. In some embodiments, the plunger includes at least two radially elastic legs, with each leg having an outside threaded section, the outside threaded sections, in combination, forming the outside thread.

In some embodiments, other means for biasing the treaded engagement in addition or alternatively to radially elastic legs may be used. Such biasing means include an inherently radially elastic outside thread or axial biasing of the threaded engagement. In some embodiments, the threaded section of the movable member is radially elastic for biasing the threaded engagement.

In some embodiments, the dosing unit includes a plunger coupler that is adapted to couple to the driving unit, where the plunger coupler transmits a driving torque about the displacement axis and slidingly engages the plunger as to rotate the plunger about the displacement axis without substantial force transmission.

Embodiments that use the plunger coupler described above also include a rotating motion of the movable member and a plunger, which displaces in a screw-like manner within the metering cavity, as described above. Where not stated differently, this embodiment is assumed in the embodiments discussed below.

In some embodiments, the plunger driver is telescopically received by the plunger or a plunger coupler, and is in axial alignment with the plunger. In other embodiments, a drive coupler of the driving unit is directly coupled to the plunger without an additional plunger coupler.

As used herein, the driving direction of the driving unit for moving the movable member into the charging valve position is referred to as "charging valve direction" while the driving direction of the driving unit for moving the movable member into the discharging valve position is referred to as "discharging valve direction", the charging driving direction and the discharging driving direction being opposite to one another.

In some embodiments, operating the driving unit in a charging driving direction results in the movable member moving into the charging valve position, followed by displacing the plunger in the distal direction, and operating the driving unit in a discharging driving direction opposite to the charging driving direction results in the movable member moving into the discharging valve position, followed by displacing the plunger in the proximal direction.

For a "valve before plunger" design, the movable member decouples upon adopting either of the charging valve position or the discharging valve position. Coupling may be achieved by stopping and/or reversing the driving direction. Embodiments of this type are in the following referred to as "valve before plunger" designs.

Here and in the following, the terms "reversing" and "reversible" generally refer to the driving direction in which a driving unit coupled to the dosing unit is operated.

In alternative embodiments, operating the driving unit in a charging driving direction results in displacing the plunger into the distal plunger end position, followed by moving the movable member in the discharging valve direction, and operating the driving unit in a discharging driving direction opposite to the charging driving direction results in displacing the plunger into the distal plunger end position, followed by moving the movable member in the discharging valve direction.

Embodiments of this type are in the following referred to "plunger before valve" designs.

For a "plunger before valve" design, the movable member couples upon the plunger, assuming either of the proximal plunger end position or the distal plunger end position, respectively, and decouples upon displacing the plunger out of the proximal plunger end position or the distal plunger end position, respectively.

The relation between the single steps of a metering sequence and the driving direction is summarized for both "valve before plunger" designs as well as "plunger before valve" designs in the following table.

| Design | Step | Sub-Sequence | Driving Direction |
|---|---|---|---|
| valve before plunger | (a) | charging sequence | charging driving direction |
| | (b) | | |
| | (c) | discharging sequence | discharging driving direction |
| | (d) | | |
| plunger before valve | (a) | charging sequence | discharging driving direction |
| | (b) | | charging driving direction |
| | (c) | discharging sequence | |
| | (d) | | discharging driving direction |

It can be seen that for "valve before plunger" designs, both the steps of the charging sub-sequence are performed with the driving unit being operated in one of the driving directions, while both steps of the discharging sequence are performed with the driving unit being operated in the other driving direction.

For "plunger before valve" designs, the driving direction is reversed between the switching step and the displacing step for both the charging sub-sequence and the discharging sub-sequence.

Both types of design involve reversing the driving direction of the drive unit to perform metering sequences. In contrast to metering units that do not involve reversing the driving direction, dosing units according to the present disclosure may be beneficial for patient safety, because the requirement for controlled reversing of the driving direction prevents the pump from continuously administering a drug in case the driving unit is permanently powered, for example because of a device defect.

A dosing unit of the "valve before plunger design" may be designed to operate as follows:

Selective coupling is achieved by transmitting a sticking friction force from the plunger and/or a plug coupled to the plunger onto the movable member. The sticking friction force may be caused by contact between adjacent components, and may, for example, be transferred from the circumferential face of a plug section onto the circumferential face of the metering section, and/or from the outer thread onto the inner thread. Accordingly, the axial position of the plunger, along the displacement axis, is maintained such that the plunger moves synchronously with the movable member when moving the movable member from the charging valve position into the discharging valve position or vice versa.

For embodiments of dosing units according to this type of design, the force and/or torque required to move the movable member is substantially smaller than the force and/or torque required to displace the plunger. The force and/or torque ratio may be in the range from 1:2 to 1:10, and is further below a maximum force and/or torque that may be transmitted from the plug onto the movable member by sticking friction.

Selective decoupling is achieved by blocking further motion of the movable member such that the movable member maintains its position while the movable member adopts the charging valve position or the discharging valve position, and the driving unit is further operated in the charging driving direction or the discharging driving direction, respectively. The blocking of further motion of the movable member may be achieved by an arrangement of stops or breaks, as described below in more detail. Blocking the movable member results in changing the interface force of the plunger and/or plug and the movable member from sticking friction engagement to sliding friction engagement.

Operation of an embodiment of a dosing unit according to this type of design may be understood according to a metering sequence as summarized in the following table.

| Step | Driving Direction | Description / Starting and Ending Position | Coupling |
|---|---|---|---|
| (d) | discharging | Starting plunger position: any position distal from proximal plunger end position, for example, a distal plunger end position; Ending plunger position: any position proximal from starting plunger position, for example, a proximal plunger end position; Movable Member: fixed in discharging valve position. | no |
| (a) | charging | Starting movable member position: discharging valve position; Ending movable member position: charging valve position. | yes |
| (b) | charging | Starting plunger position: ending plunger position of step (d), above; Ending plunger position: any position distal from starting plunger position, for example, a charged plunger; Movable member: fixed in charging valve position. | no |
| (c) | discharging | Starting movable member position: charging valve position; Ending movable member position: discharging valve position. | yes |

Further aspects, as well as alternative "valve before plunger" designs, are described below in greater detail.

A dosing unit of the "plunger before valve" design may be designed in a similar way as described above. However, the force and/or torque required to move the movable member is substantially larger than the force and/or torque required to displace the plunger, and is further below a maximum force and/or torque that may be transmitted onto the movable member as sticking friction force. The force and/or torque required for moving the movable member may be adjusted by adjusting the valve sealing force between the movable member and the stationary member or an additional bearing friction force of the movable member.

For embodiments of dosing units according to this type of design, the movable member is decoupled from the plunger and/or a plug coupled to the plunger such that the movable member maintains its position so long as the plunger does not adopt either the proximal plunger end position or the distal plunger end position. Coupling is achieved by blocking further displacement in the proximal direction if the plunger adopts the proximal plunger end position and by blocking further displacement in the distal direction if the plunger adopts the distal plunger end position. The blocking may be achieved by an arrangement of stops and/or blocks. In some embodiments, blocking is achieved by the outside thread of the plunger contacting an end of inside thread of the metering cavity. If further displacement of the plunger is blocked, the plunger maintains its position along the displacement axis and moves synchronously with the movable member when moving the movable member from the charging valve position into the discharging valve position or vice versa.

It should be noted that for embodiments of dosing units according to this type of design, the force and/or torque required to move the movable member is, at least in part, transmitted onto the movable member by axial contact force resulting from exerting a force and/or torque onto the plunger that forces the plunger in a blocked displacing direction.

For some embodiments of dosing units, such as the "valve before plunger" design described above, switching between a charging sub-sequence and a discharging sub-sequence is possible at any position of the plunger between the proximal plunger end position and the distal plunger end position by reversing the driving direction. With embodiments of this design, the metering cavity may be fully charged to the maximum metering volume whenever required. This may be beneficial, for example, if a drug bolus that exceeds the current metering volume resulting from the current position of the plunger has to be administered to a patient.

For alternative embodiments, such as the "plunger before valve" design described above, switching between the charging sequence and the discharging sequence by reversing the driving direction is possible only if the plunger is in one of the proximal plunger end position or the distal plunger end position. For embodiments of dosing units according to this type of design, a drug bolus that exceeds the current metering volume resulting from the current plunger position may be administered in two or more steps, between which the metering cavity is recharged to the maximum metering volume.

In some embodiments, the dosing unit includes an arrangement of stationary stops and movable stops, where the movable member decouples from the plunger when a movable stop engages a corresponding stationary stop, and the movable member couples to the plunger when a movable stop disengages a corresponding stationary stop.

For some embodiments, the movable member includes two rigid movable stops made, e.g., by one or multiple cams, which may be arranged, for example, at the outer face of the movable member or at the proximal front or the distal front of the movable member. The rigid movable stops are adapted to engage two corresponding stationary stops such that the movable member is limited to rotate between its charging valve position and its discharging valve position. In alternative embodiments, the movable stops are formed by end pieces of at least one spring, the spring belonging to a wrap spring clutch, as will be described below in greater detail.

In some embodiments, the movable member is adapted to selectively couple the plunger by radial and/or axial contact force. Some embodiments involving selective coupling by radial and/or axial contact force are the "valve before plunger" design and the "plunger before valve" design described above, and which are further described below.

In some embodiments, radial and/or axial contact force is controlled based on the axial position of the plunger in the metering cavity and/or in based on the position of the movable member with respect to the stationary member.

One embodiment for a dosing unit with controlled axial contact force is the "plunger before valve design" as described above, and which further designs are described below.

Controlling radial and/or axial contact force may be beneficial because it avoids relying only on the contact force, in particular radial contact force as defined by design factors such as material combination and dimensions for moving the movable member, and therefore increases robustness and reliability, in particular under the aspect of large scale manufacture.

In some embodiments involving controlled radial contact force, radial contact force is controlled by controlling a radial dimension of the plunger.

In some embodiments, the radial dimension of an outside thread is controlled by selective radial deflection of the at least one leg. Therefore, the plunger includes a plunger shaft with at least one plunger shaft cam, the at least one plunger shaft cam being adapted to selectively engage at least one proximal plunger coupler cam of a plunger driver if the plunger adopts the proximal plunger end position, and to selectively engage at least one distal plunger coupler cam of a plunger driver if the plunger adopts the distal plunger end position, where the engagement increases the contact force between the movable member and the plunger.

The plunger may include an elongated plunger shaft that includes radially elastic legs with outer threads as described above. Plunger shaft cams are provided at the distal end sections of the legs in radial alignment with the outer threads. The plunger coupler includes an elongated plunger coupler shaft, which may be telescopically received by the plunger, and includes the plunger coupler cams, where the at least one proximal plunger coupler cam is located at the proximal end of the plunger coupler shaft and the distal plunger coupler cam is located at the distal end of the plunger coupler shaft. The plunger coupler cams may be ramp-like in order to allow smooth engagement.

By an engagement of the at least one proximal plunger coupler cam with the at least one plunger shaft cam, the at least one leg of the plunger shaft is radially deflected towards the circumferential inside face of the metering cavity, thus increasing the contact force of the threaded engagement, when the plunger is in the proximal plunger end position, i.e., in its most proximal position.

By an engagement of the at least one distal plunger coupler cam with the at least one plunger shaft cam, the at least one leg of the plunger shaft is radially deflected towards the circumferential inside face of the metering cavity, thus increasing the contact force of the threaded engagement, when the plunger is in the distal plunger end position, i.e., in its most distal position.

In some embodiments, the plunger shaft includes at least two legs, each leg including a plunger shaft cam, and the plunger coupler shaft includes an identical number of corresponding proximal plunger coupler cams and distal plunger coupler cams.

For embodiments of dosing units according to this type of design, as well as for embodiments that include controlled axial contact force as described above, releasing the contact force after performing a valve switching step requires considerable force and/or torque, which may be provided by the driving unit. This force and/or torque peak may be evaluated as force and/or torque feedback.

In some embodiments, the dosing unit comprises a wrap spring clutch, the wrap spring clutch selectively decoupling the movable member when the movable member adopts either of its charging valve position or its discharging valve position.

A spring of the wrap spring clutch may be arranged in a distal clutch section of the metering cavity and in axial alignment with the displacement axis. Alternatively, a spring of the wrap spring clutch is arranged outside the metering cavity. A spring of the wrap spring clutch may include the movable member.

In some embodiments that include a wrap spring clutch, a spring of the wrap spring clutch selectively couples a plunger coupler and the movable member. The spring may be wrapped around a distal plunger coupler section, the distal plunger coupler section and the spring being designed such that the windings of the spring are in sticking friction engagement with the distal plunger coupler section due to radial contact force. The plunger coupler further includes a proximal plunger coupler section, the proximal plunger coupler section being adapted to transmit a driving torque onto the plunger and to be in sliding axial engagement with the plunger. The spring is further attached to and/or in force transmission engagement with the movable member.

In some embodiments involving a wrap spring clutch, one end section of a spring of the wrap spring clutch acts as movable charging stop and another end section of a spring of the wrap spring clutch acts as movable discharging stop, the movable charging stop being adapted to engage a stationary charging stop when the movable member adopts the charging valve position and the movable discharging stop being adapted to engage a stationary discharging stop when the movable member adopts the discharging valve position, thus decoupling the movable member.

The movable charging stop and the movable discharging stop may be straight end sections of a coil spring which are arranged in axial alignment with the displacement axis. The end sections may project out of the metering cavity in a radial direction through a clutch aperture in the circumferential wall of the metering cavity, and the stationary stops are arranged outside the movable member. Upon either of the movable stops engaging the corresponding stationary stop, the core diameter of the spring is elastically widened, thus reducing contact force and changing the sticking friction engagement with the plunger coupler into a sliding friction engagement and decoupling the movable member.

Further aspects of designs of dosing units including a wrap spring clutch, as well as its operation, are described below in the framework of one embodiment.

In some embodiments, the dosing unit includes or is adapted to couple to a movable member position detection unit and/or a plunger position detection unit. A movable member position detection unit may be provided and used to detect if the movable member is in either of its charging valve position or its discharging valve position for controlling the driving unit of the infusion pump and/or as additional safety element. For this purpose, arrangements known in the art, such as electro-mechanical end switches, electrical contacts or light barriers, may be used. In a similar way, a plunger position detection unit may be provided and used to detect if the plunger is in either of the distal plunger end position or the proximal plunger end position. A plunger position detection unit may further be adapted to determine the position of the plunger between the charging plunger valve position and its discharging valve position, and may be provided for the same purposes as a movable member position detection unit. For this purpose, a plunger position detection unit may comprise sensors known in the art, such as variable resistors, CCD sensors or position detection sensors (PDSs) and a corresponding processing circuit.

In order to detect the occurrence of valve leakages, the dosing unit may include or is operatively coupled to at least one valve leakage detector. Valve leakage detectors may be utilized by providing electrical circuits that are generally open and are closed by a conductive drug, such as insulin, in case of a leakage. In some embodiments, both a charging valve leakage detector and a discharging valve leakage detector are provided.

In a further aspect, the present disclosure is directed towards a fluidic assembly, including:

a) a dosing unit as described above; and
b) a drug reservoir, the drug reservoir being in fluidic connection with the inlet valve of the dosing unit.

The dosing unit and the drug reservoir may be designed as integral unit. In some embodiments, the dosing unit and the drug reservoir are designed to be a disposable item that is discarded after emptying the drug reservoir. In alternative embodiments, the drug reservoir is adapted to be refilled, e.g., via a septum.

The drug reservoir may be of any design known in the art for this type of application and may, for example be realized as a cylindrical cartridge, a bag, a pouch, or the like. In some embodiments, the drug reservoir is a bag that may additionally be spring-loaded.

In a further aspect, the present disclosure is directed towards an ambulatory infusion device. An ambulatory infusion device according to the present disclosure includes:

a) a reversible driving unit;
b) a drug reservoir, the drug reservoir being adapted to comprise the liquid drug;
c) a dosing unit as described above, the charging valve of the dosing unit being in fluidic connection with the drug reservoir, the dosing unit being coupled to the driving unit;
d) an outlet assembly in fluidic connection with the discharging valve of the dosing unit; and
e) a controller unit adapted to control the driving unit for drug infusion over the extended time period.

The reversible driving unit may include a rotary drive such as a DC motor, a brushless DC motor or a stepper motor, and may further include a reduction gear. The reversible drive may further include drive sensors such as optical encoders, hall encoders and/or a revolution speed sensor. The reversible driving unit may include a drive coupler, the drive coupler being adapted to transmit a driving force and/or torque to the dosing unit.

The term "outlet assembly" refers to any element or a combination of elements downstream from the dosing unit and being adapted for fluidic connection with the outlet valve of the dosing unit. In particular, the outlet assembly may include a subcutaneous infusion cannula and/or a fluidic element to be coupled to an infusion cannula and a dosing unit according to the present disclosure, such as an infusion line, an infusion line connector, a check valve, a pressure measurement unit, or the like.

The controller unit may include components known in the art such as microcontrollers, ASICS, volatile and/or non-volatile memory components, and the like. The controller unit may be coupled to and/or include a user interface, such as push buttons, a display, audio and/or tactile indicators, and the like. The controller unit may include or is operatively coupled to at least one communication interface such as an IR interface and/or an RF interface.

The ambulatory infusion device may further include at least one power supply such as a rechargeable and/or a non-rechargeable battery.

The ambulatory infusion device may include a housing, which may be a single housing enclosing all components and/or may be made of more than one housing adapted to physically and/or operatively couple to each other. For example, the housing may be made of a first housing enclosing durable components such as the controller unit, that drive a user interface, and the like, while disposable components, for example the dosing unit and the drug reservoir, are enclosed by a second housing. For embodiments according to this type of design, the power supply may included in either of the first housing or the second housing.

In some embodiments, the dosing unit is, at least in part, integral with the drug reservoir and/or the output unit.

The ambulatory infusion device may, at least in part, include sensors and/or detection units such as movable member position detection units and/or a plunger position detection unit as described above, a drive force and/or torque sensor, a fluidic pressure sensor and the like. A force and/or torque sensor may be employed for detecting the plunger traveling to either of the distal plunger end position and the proximal plunger end position, as well as the movable member traveling to either of its charging valve position or its discharging valve position, because the occurrence of these situations is associated with a jump and/or peak in the driving force. Additionally or alternatively to force and/or torque measurement, the current supplied to a drive motor may be evaluated as a measure of the driving force and/or torque.

The dosing unit and the outlet assembly may be disposable units and may have a typical lifetime of a few days, after which they are discarded and replaced. The other components of the device are durable and have a longer lifetime of, for example, some years, or a generally open and unlimited lifetime.

An ambulatory infusion device according to the present disclosure may be designed for the therapy of diabetes mellitus by CSII therapy. For this application, the drug reservoir may be adapted to store the insulin amount required, for example, for, one week of therapy, which may be in the range of 200 to 500 IU (International Units), corresponding to 2 to 5 ml of insulin in the concentration U100. However, larger or smaller drug volumes and/or drug concentrations may be used as well.

Further capabilities and aspects of an ambulatory infusion device for diabetes therapy, while not explicitly mentioned, may be obvious for such devices for a person ordinary skilled in the art. Besides diabetes therapy, ambulatory infusion devices according to the present invention may be used for therapies such as cancer therapy or pain therapy without substantial modifications.

According to a still further aspect of the present disclosure, the disclosure is directed towards a method for operating a metering unit for an ambulatory infusion device, the method including the steps of:

a) providing a dosing unit and a driving unit;
b) coupling a plunger of the dosing unit, the plunger being located, at least in part, in a metering cavity of a movable member of the metering unit and being adapted for displacement in the metering cavity along a displacement axis;
c) coupling the movable member of the dosing unit to the driving unit with the plunger being further coupled to the driving unit;
d) moving the movable member into a charging valve position with a position of the plunger relative to the movable member along the displacement axis being maintained;

e) decoupling the movable member from the driving unit (505) with the plunger being further coupled to the driving unit;

f) displacing the plunger along the displacement axis in a distal direction with the position of the movable member being maintained, thus charging the metering cavity;

g) coupling the movable member of the dosing unit with the driving unit, with the plunger being further coupled to the driving unit;

h) moving the movable member into a discharging valve position, with the position of the plunger relative to the movable member along the displacement axis being maintained;

i) decoupling the movable member from the driving unit with the plunger being further coupled to the driving unit; and k) displacing the plunger along the displacement axis in a proximal direction with the position of the movable member being maintained, thus discharging the metering cavity.

In some embodiments, the steps (d) to (k) of the method are preformed in a cyclic manner and after performing the steps (a) to (c). Further aspects of the method, as well as embodiments for carrying out the method, are described above in the framework of a dosing unit according to the present disclosure.

In some embodiments, the method includes performing the steps (d) and (f) by operating the driving unit in a charging driving direction and performing the steps (h) and (j) by operating the driving unit in a discharging driving direction, the charging driving direction being opposite to the discharging driving direction. Carrying out the method according to this embodiment corresponds to a "valve before plunger" design of the dosing unit, as described above.

In alternative embodiments, the method includes performing the steps (f) and (h) by operating the driving unit in a charging driving direction and performing the steps (j) and (d) by operating the driving unit in a discharging driving direction, the charging driving direction being opposite to the discharging driving direction. Carrying out the method according to this embodiment corresponds to a "plunger before valve" design of the dosing unit, as described above.

In the following, exemplary dosing units in accordance with the present inventions which may be used in ambulatory infusion devices according to the present disclosure, corresponding methods for controlling operation of a dosing unit according to the present disclosure and an embodiment of the ambulatory infusion device according to the present disclosure are described with reference to the figures.

Figure 1:
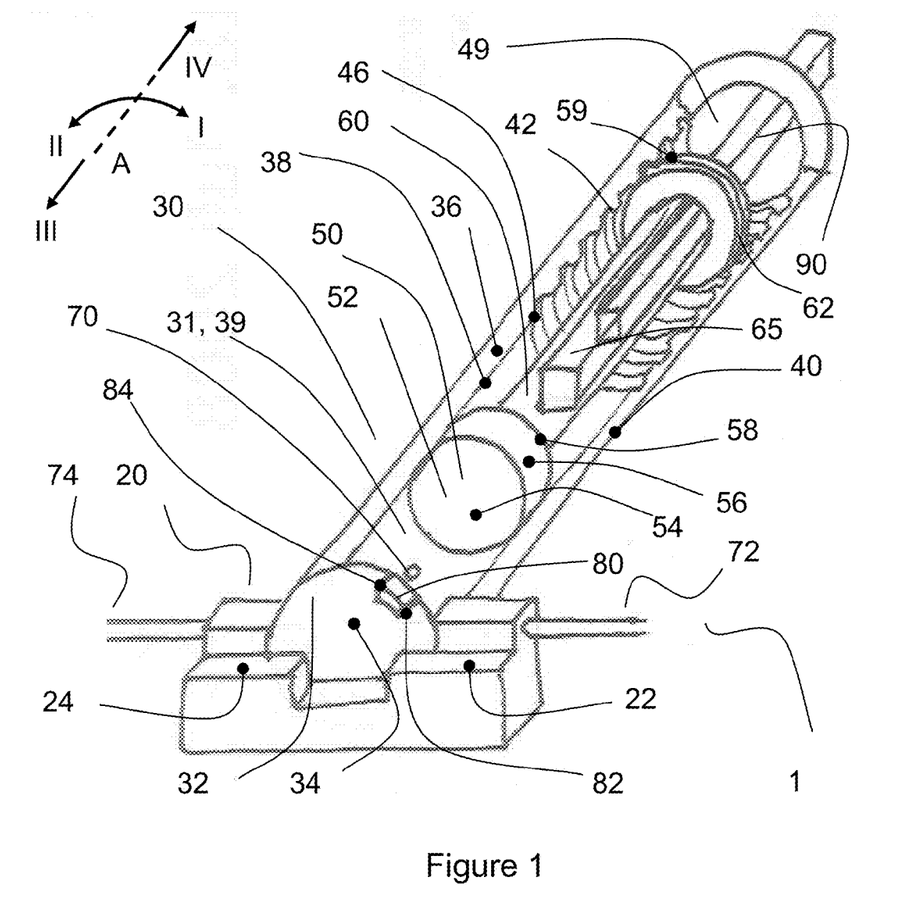
FIG. 1 depicts a schematic view of a dosing unit according to one or more embodiments of the present disclosure.

FIG. 1 depicts a dosing unit 1 according to one embodiment of the disclosure in a local section isometric view, with the circumferential wall 36 being partly cut away such that the elements located inside the metering cavity 31 are more clearly visible.

The dosing unit 1 includes a movable member 30 and a stationary member 20. The movable member 30 substantially has the shape of a hollow cylinder having a closed proximal front 34 and an open distal front 49. The movable member 30 further has a circumferential wall 36 and a proximal front wall 32 such that it forms a hollow cylinder, the inner volume of which forms the metering cavity 31. The displacement axis A is the axis of symmetry of the movable member (shown in FIG. 1 shifted parallel to for purposes of clarity).

The movable member 30 is rotationally supported by the stationary member 20. A bearing is formed, in combination, by the circumferential outer face 40 of the circumferential wall 36, the proximal front 34 and a bearing surface (not visible) of the stationary member 20. The dimensions and tolerances of the movable member 30 and the stationary member 20 are such that the contacting area of the circumferential outer face 40 and the bearing surface of the stationary member 20, in combination, form a fluid-tight seal. The movable member 30 and/or the stationary member 20 may have some radial elasticity in order to ensure sealing. Alternatively, both the movable member 30 and the stationary member 20 are made from generally "hard" materials, e.g. as injection-molded plastic components, where one of the movable member 30 or the stationary member 20 is harder than the other for optimal sealing.

A movable cam 80 projects from the proximal front 34 in proximal direction III, the movable cam 80 having a movable charging stop 82 and a movable discharging stop 84 formed by faces of the movable cam 80. The movable charging stop 82 engages a stationary charging stop 22 when the movable member is in its charging valve position and the movable discharging stop 84 engages a stationary discharging stop 24 when the movable member is in its discharging valve position. The stationary stops 22, 24 are formed by faces of the stationary member 20. In combination, the stops 22, 24, 82, 84 limit the rotation of the movable member 30 between the charging valve position and the discharging valve position.

A movable valve aperture 70 passes through the circumferential wall 36 of the movable member 30 in proximity to the proximal front 34.

A charging connector 72 creates a fluid connection between the stationary member 20 and a drug reservoir (not shown) and a discharging connector 74 creates a fluid connection between the stationary member 20 and an outlet assembly (not shown). The charging connector 72 and the discharging connector 74 are inserted into a corresponding charging valve bore (not visible) and discharging valve bore (not visible) of the stationary member 20, the valve bores forming stationary valve apertures. The position of the bores in the stationary member 20 are such that the movable valve aperture 70 is in alignment with the corresponding charging valve bore when the movable member 10 is in its charging valve position, and the movable valve aperture 70 is in alignment with the discharging valve bore when the movable member 30 is in its discharging valve position. In order to reduce the requirements for tight manufacturing tolerances, the dimensions of the stationary valve apertures, that is, the diameters of the valve bores where contacting the circumferential outer face 40 of the movable member 30, may be somewhat larger than the diameter of the movable valve aperture 70. Further, the valve bores may be chamfered in locations proximate to the movable member 30.

A plunger 50 is located inside the metering cavity 31. The plunger 50 includes an elongated plunger shaft 60 (shown transparent in FIG. 1). The plunger shaft 60 adjoins a plug 52 and projects from the distal plug front 58 in distal direction IV. The plunger shaft 60 includes an outside thread 62 near its distal end. The plug 52 and the plunger shaft 60 may be integrally formed by injection molding, but may also be assembled from a number of components. The outside thread 62 of the plunger shaft 60 is in threaded and substantially play-free engagement with a corresponding inside thread 42 of a distal section of the metering cavity 31. The length that the inside thread 42 extends along the metering cavity 31 is determined by the required plunger displacement distance. The section of the metering cavity 31 located in the proximal direction III from the inside thread 42 is the metering section 39.

In the distal plunger end position, the distal plug front 58 adjoins the distal end 46 of the metering section 39. While not shown, a further stop may be provided at the distal front 49 which engages the distal shaft end 59 in the distal plunger end position as to limit the travel of the plunger 50 in the distal direction IV. In the proximal plunger end position, the proximal plug front 54 substantially adjoins the inner face (not visible) of the proximal front wall 32 of the movable member 30.

Axial translation of the plunger 50 is accordingly limited between the distal plunger end position and the proximal plunger end position with the plug 52 being located in the metering section 39 of the metering cavity 31. The proximal plug front 54, the circumferential face 38 of the metering section 39 and the inner surface (not visible) of the proximal front wall 32, in combination, form the variable metering volume.

The plunger shaft 60 comprises an elongated coupler hole 65 of square cross section, which is adapted to telescopically receive a drive coupler 90 of a reversible driving unit (further components of driving unit not shown), such that the drive coupler 90 transmits a driving torque onto the plunger 50 but is in axial sliding engagement with the plunger 50.

Coupling of the movable member 30 is performed by transmitting a sticking friction force from the circumferential face 56 of the plug 52 onto the circumferential face 38 of the metering section and from the outside thread 62 onto the inside thread 42.

A dosing unit 1 according to this embodiment may be designed as either of "valve before plunger" or "plunger before valve" design. If the torque required for rotating the movable member between the charging valve position and the discharging valve position is below the torque required for displacing the plunger, the dosing unit 1 acts is a "valve before plunger" design; otherwise it is a "plunger before valve" design.

The description as given above is a "valve before plunger" design. For a "plunger before valve design", the role of the inlet valve and the outlet valve, and thus of the charging tube and the discharging tube, are reversed. That is, for a "plunger before valve design" element number 74 refers to the inlet tube and element number 72 to the outlet tube.

For a "valve before plunger" design, changing between a charging sub-sequence and a discharging sub-sequence may be performed by reversing the driving direction for any plunger position.

For a "plunger before valve" design, changing between a charging sequence and a discharging sequence is possible only if the plunger is in either of its end positions, that is, in the distal plunger end position or the proximal plunger end position, respectively.

For both designs, it is assumed that the torque required for rotating the movable member 30 within the stationary member 20 does not exceed a maximum force that may be transmitted via sticking friction.

Several variations of this embodiment may be obvious for a person skilled in the art. For example, the cross-section of the cross section of the drive coupler 90 and the coupler hole 65 may be different from square, the movable valve aperture 70 may be provided at the proximal front wall 32, the arrangement of stops may be different, and the like.

Figure 2:
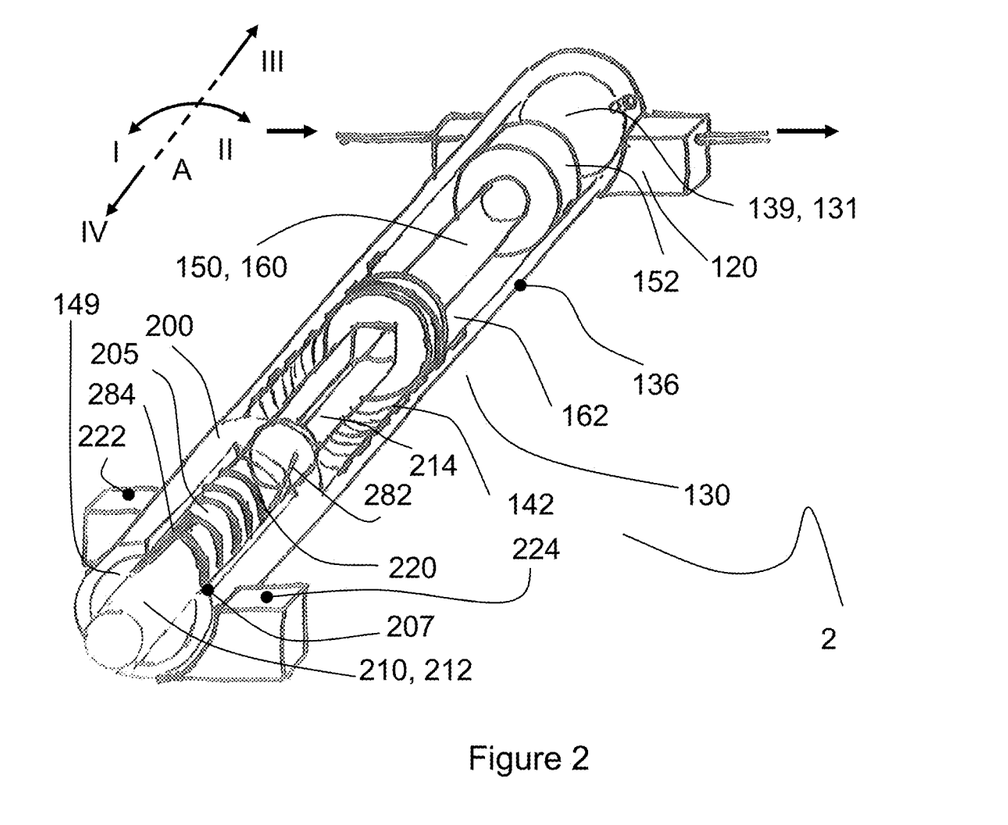
FIG. 2 depicts a schematic view of a dosing unit according to one or more embodiments of the present disclosure.

FIG. 2 shows another embodiment of a dosing unit 2 according to the present disclosure in a view similar to FIG. 1. The aspects of this embodiment that differ from the embodiment shown in FIG. 1 and described above are primarily discussed below. It should be noted that in contrast to FIG. 1, FIG. 2 depicts the dosing unit from the distal side, that is, from the drive side.

With respect to the bearing, the movable member 130 and the valve apertures, the design of the stationary member 120 is analogous to the stationary member 20 described above in regard to FIG. 1. However, an arrangement of stationary stops is not provided at the stationary member 120 depicted in FIG. 2.

While the inside thread 142 and the metering section 139 of the metering cavity 131 depicted in FIG. 2 are designed as described above in regard to FIG. 1, the movable member 130 further comprises a clutch section 200 located in a distal direction IV from the inside thread 142. In the clutch section 200, the circumferential wall 136 of the movable member 130 comprises an elongated clutch aperture 205 that extends in axial direction, the distal clutch aperture end 207 adjoining the distal front 149 of the metering cavity 131 and thus the distal front of the circumferential wall 136.

The plunger 150 comprises a distal outer thread 162, an elongated plunger shaft 160, and a proximal plug section 152.

A plunger coupler 210 is provided, the plunger coupler 210 having a circular distal plunger coupler section 212 in the area of the clutch aperture 205 and a proximal plunger coupler section 214 is received by a coupler hole of square cross section (not visible in FIG. 2) of the plunger 150 of square or generally non-linear cross section. The proximal plunger coupler section 214 fulfills the same function as the drive coupler 90 of the exemplary embodiment as described above in regard to FIG. 1. The distal plunger coupler section 212 is adapted to couple to a drive coupler (not shown) of a reversible driving unit. The plunger coupler 210 is adapted to perform a rotary motion but to stay in place in an axial direction relative to the movable member 130.

A coil spring 220 is wrapped around the distal plunger coupler section 212, where the length of the coil spring 220 and the axial position of the coil spring 220 on the distal plunger coupler section 212 are such that the distance between the proximal spring end 282 and the distal spring end 284 is less than the depth of the clutch aperture 205. The internal diameter of the coil spring 220 is such that the windings of the coil spring 220 are in frictional sticking contact with the distal plunger coupler section 212, i.e., prior to installation, the internal diameter of the coil spring 220 is somewhat smaller than the diameter of the distal plunger coupler section 212. At approximately the middle of its length, the coil spring 220 is further fixed to the inner circumferential face of the movable member 130 (fixture not visible), such that a force and/or torque can be transmitted from the plunger coupler 210 onto the movable member 130 via the coil spring 220, resulting in the movable member 130 being rotationally coupled to the plunger coupler 210. The coil spring 220 may have three to ten windings, but may also have less windings and even have less than one complete winding.

The proximal spring end 282 and the distal spring end 284 radially project out of the clutch aperture 205. The proximal spring end 282 acts as a movable charging stop and the distal spring end 284 acts as a movable discharging stop. The proximal spring end 282, acting as the movable charging stop, may engage a stationary charging stop 222 and the distal spring end 284, acting as the movable discharging stop, may engage a stationary discharging stop 224.

If either of the movable stops 282, 284 engages the corresponding stationary charging or discharging stop 222, 224, providing further driving torque to the plunger coupler 210 results in the windings of the coil spring 220 being widened (i.e., at least partially unwound), resulting in the coil spring 220 and the distal plunger coupler section 212 changing from sticking friction engagement to sliding friction engagement, thus rotationally decoupling the movable member 130 from the plunger coupler 210.

For this embodiment, the movable member 130 is in the decoupled state if the movable member 130 is in either of the charging valve position or the discharging valve position and in the coupled state otherwise. Reversing the driving direction of the plunger coupler 210 results in the engagement of a movable stop (i.e., the proximal and distal spring ends 282, 284) and a corresponding stationary charging or discharging stop 222, 224, to be released, thus rotationally coupling the movable member 130 to the plunger coupler 210.

As can been seen from the description, this dosing unit 2 depicted in FIG. 2 acts as "valve before plunger" design and allows for changing between a charging sub-sequence and a discharging sub-sequence at any plunger position by reversing the driving direction of the plunger coupler 210. However, unlike a "valve before plunger design" according to FIG. 1, the embodiment depicted in FIG. 2 does not rely on plunger friction and/or thread friction for moving the movable member.

Several variations of this embodiment may be obvious for a person skilled in the art. For example, instead of one coil spring 220 that is fixed to the movable member 130 near the middle of its length, two separate coil springs may be used. In alternative embodiments employing one coil spring 220, the coil spring 220 is not fixed to the movable member 130. Instead, engagement of the movable charging stop, i.e., the proximal spring end 282, or the movable discharging stop, i.e., the distal spring end 284, with the edges of the clutch aperture 205 may be used for force and/or torque transmission from the plunger coupler 210 to the movable member 130. Furthermore, the distal plunger coupler section 212 may not be circular, but instead include a cross section having a different shape that allows transmitting a sticking friction force onto the coil spring 220, such as a hexagon cross section.

Figure 3A:
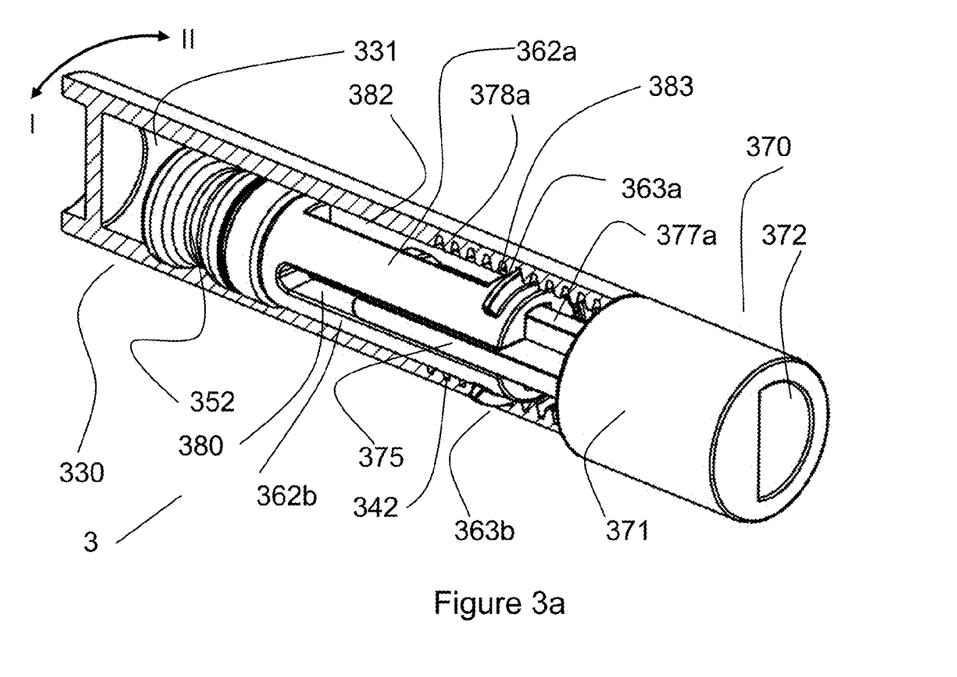
FIG. 3a depicts a schematic view of a movable member and a plunger of a dosing unit according to one or more embodiments of the present disclosure.
Figure 3B:
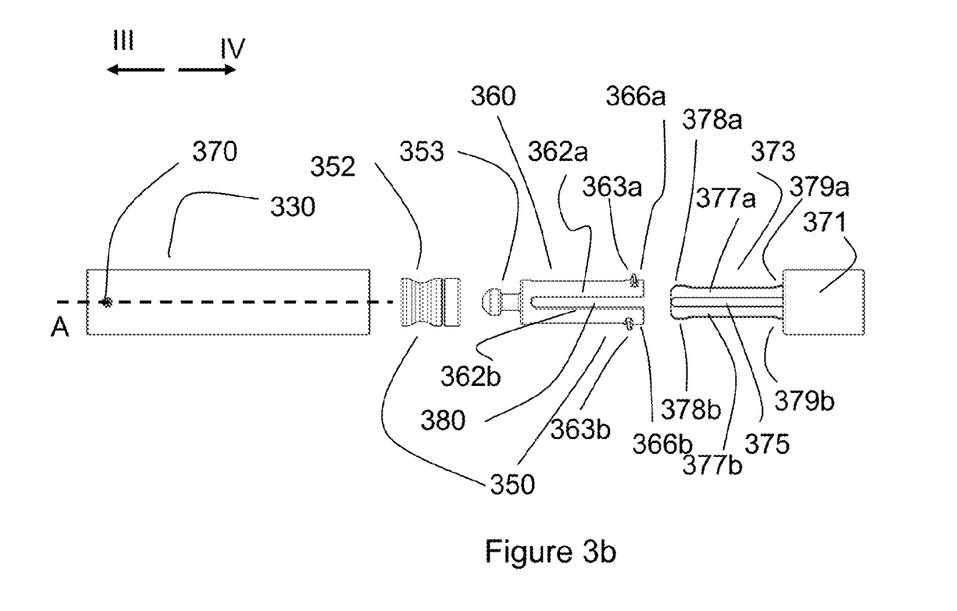
FIG. 3b depicts a schematic view of a movable member and a plunger of a dosing unit according to one or more embodiment.

FIG. 3a and FIG. 3b show a dosing unit 3 according to a still further exemplary embodiment of the present invention. FIG. 3a shows the movable member and the plunger in a perspective partial section view, while FIG. 3b shows an exploded view of the dosing unit 3 depicted in FIG. 3a. As discussed below, reference is made to both FIG. 3a and FIG. 3b. The stationary member of this embodiment is not shown and may be designed in an analogue way to the previously described embodiments.

The movable member 330 including the movable valve aperture, here the plunger coupler 370, and the metering cavity 331 may be designed in an analogue way to the previously described embodiments depicted in FIGS. 1 and 2. The plunger 350 includes a plug 352 and an elongated plunger shaft 360. The plunger shaft 360 and the plug 352 are coupled to one another by a plug coupler 353 located at the proximal end of the plunger shaft 360 and a corresponding aperture (not visible) in the distal front of the plug 352. Alternatively, the plug 352 may be integral with the plunger shaft 360.

The plunger coupler 370 includes a coupler body 371, the coupler body 371 abuts the movable member 330 along the distal end of the movable member 330 and includes a coupler aperture 372 of non-circular cross-section. The coupler aperture 372 is adapted to engage a drive coupler (not shown) of a driving unit (not shown) of the infusion device.

The plunger coupler 370 includes an elongated plunger coupler shaft 373 that extends in a proximal direction from the coupler body 371, where the length of the plunger coupler shaft being 373 is defined by the required plunger displacement distance.

The plunger coupler shaft 373 has a cross-like cross section with four elongated protrusions. Two of the opposing protrusions are force and/or torque transmission protrusions. FIG. 3a shows one of the force and/or torque transmission protrusions 375; the second one is hidden in this view. The other two opposing protrusions are cam protrusions 377a, 377b, the function of which is described below. The cam protrusions 377a, 377b include ramp-like proximal plunger coupler cams 378a, 378b and distal plunger coupler cams 379a, 379b located at the proximal and distal end of the plunger coupler shaft 373, respectively.

The elongated plunger shaft 360 includes two elongated and radially elastic legs 362a, 362b. The legs 362a, 362b have distal outside threads 363a, 363b that are in threaded engagement with an inside thread 342 of the movable member 330. Between the legs 362a, 362b, force and/or torque transmission slits 380 are provided. FIG. 3a and FIG. 3b depict one of the force and/or torque transmission slits 380; the second force and/or torque transmission slit is hidden in this view. The plunger shaft 360 is designed such that the legs 362a, 362 are slightly inwardly deflected by the threaded engagement, such that a radial biasing force is exerted by the outside thread 363a, 363b onto the inside thread 342, resulting in a play-free threaded engagement. Because the length of the outside thread 363a, 363b is only one winding, the biasing force is substantially constant over the length of the threaded engagement. The force and/or torque transmission slits 380 receive and slidingly engage the force and/or torque transmission protrusions 375, such that the force and/or torque transmission protrusions 375 are telescopically received by the plunger shaft 360.

The plunger shaft 360 comprises two cam receiving slits. FIG. 3a shows one of the cam receiving slits 382, the second one is hidden in this view. The cam receiving slits 382 slidingly receive the cam protrusions 377a, 377b. The cam receiving slits 382 do not extend over the full length of the legs 362a, 362b. In particular, the distal ends 383 of the cam receiving slits 382 are located in a proximal direction III from the outside threads 363a, 363b.

If the plunger 350 is located in neither of the distal plunger end position, nor the proximal plunger end position, the proximal plunger coupler cams 378a, 378b are slidingly received by the cam receiving slits 382 without a radial force being exerted on the proximal plunger coupler cams 378a, 378b. Therefore, the plunger 350 may be displaced with the movable member 330 being decoupled from the plunger coupler 370.

If the plunger 350 adopts the distal plunger end position, the distal plunger coupler cams 379a, 379b engage the plunger cams 366a, 366b, the plunger cams 366a, 366b being made of the distal portions of the legs 362a, 362b in radial alignment with the outside threads 363a, 363b. In an analogue way, if the plunger 350 adopts the proximal plunger end position, the proximal plunger coupler cams 378a, 378b engage the plunger cams 366a, 366b. Due to the cam engagement, the legs 362a, 362b are deflected outwards. In doing this, the contact force between the outside threads 363a, 363b and the inside thread 342 is increased, such that the movable member 330 is coupled to the plunger coupler 370.

Even though not shown, an arrangement of movable stops at the movable member 330 and of stationary stops is provided such that the movable member 330 is limited to rotate between its charging valve position and its discharging valve position, as described above in regard to FIGS. 1 and 2.

Because the movable member 330 is coupled to the plunger coupler 370 only if the plunger 350 is positioned in either of the distal plunger end position or in the proximal plunger end position, switching between a charging sub-sequence and a discharging sub-sequence may be performed only in this end positions of the plunger 350.

A dosing unit 3 according to this embodiment is a "valve before plunger" design. Switching from a valve switching step to a plunger displacing step may involve a considerable amount of force, because the contact force between the outside thread 363a, 363b, and the inside thread 342 has to be first released. For a "valve before plunger", design, the movable member 330 is further forced in the charging valve direction if the movable member 330 has previously been rotated into the charging valve position and is forced in the discharging valve direction if the movable member has previously been rotated into the discharging valve position. Further rotation of the movable member, however, is blocked by the stop arrangement (not shown).

Figure 4:
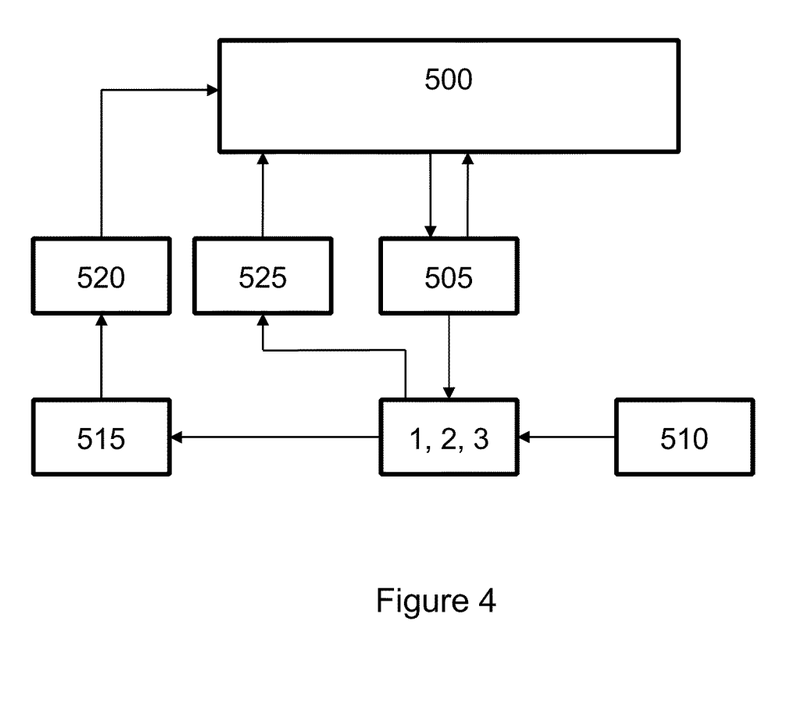
FIG. 4 depicts a schematic view of an ambulatory infusion device according to one or more embodiments of the present disclosure.

FIG. 4 shows a schematic structural view of an ambulatory infusion device according to the present disclosure. The dosing unit 1, 2, 3 of the infusion device may be any dosing unit according to the present disclosure as described above. The dosing unit 1, 2, 3 is coupled to a driving unit 505, which includes a rotary electric drive, for example, a DC motor, a brushless DC motor or a stepper motor, and further includes a drive coupler that transmits a driving torque onto the dosing unit 1, 2, 3 as described above. The driving unit 505 may further include intermediate drive components such as a reduction gear.

The driving unit 505 receives it electrical power and control signals from the controller unit 500. The driving unit 505 may further include sensor elements such as a rotational encoder for feeding one or multiple feedback signals into the controller unit 500. The driving unit 505 may include a torque and/or a force sensor for measuring the torque transmitted into the dosing unit 1,2,3. For this purpose, the driving unit 505 may, fully or in part, be floating relative to the dosing unit 1, 2, 3, as known in the art. The controller unit 500 may further be adapted to measure the drive current as a measure for the torque transmitted into the dosing unit 1, 2, 3.

The dosing unit 1, 2, 3, is in fluidic connection with a drug reservoir 510, for example, a spring-loaded bag, and an output assembly 515 that includes a subcutaneous cannula.

A movable member position detector 525 is coupled to or is included within the dosing unit 1, 2, 3, and includes electrical contacts and/or light barriers that detect if the movable member of the dosing unit 1, 2, 3 is in the charging valve position or the discharging valve position.

The infusion device further includes an optional administration supervising unit 520, which is operatively coupled to the output assembly 515 and provides supervising information to the controller unit 500. The administration supervising unit 520 may include a fluidic pressure measurement unit as known in the art for measuring and monitoring the fluidic outlet pressure. By monitoring the fluidic outlet pressure, a number of potentially hazardous situations, for example occlusions, may be detected, as known in the art.

Further typical elements of ambulatory infusion devices such as power supplies, user interface data interfaces, and the like are not shown in FIG. 4, but may be present in the ambulatory infusion devices.

What is claimed is:

The invention claimed is:

1. A dosing unit for an ambulatory infusion device, comprising:
    a stationary member;
    a movable member, the movable member and the stationary member, in combination, making a charging valve and a discharging valve, the charging valve being adapted to be in fluid communication with a drug reservoir and the discharging valve being adapted to be in fluid communication with an outlet assembly, wherein the movable member is movable between a charging valve position, in which the charging valve is open and the discharging valve is closed, and a discharging valve position, in which the discharging valve is open and the charging valve is closed; and
    a plunger, located, at least in part, in a metering cavity of the movable member and being adapted for displacement in the metering cavity along a displacement axis between a distal plunger end position and a proximal plunger end position;
    wherein the plunger is adapted to couple continuously to a driving unit and the movable member is adapted to selectively couple and decouple to the driving unit, such that, by operating the driving unit with the movable member being coupled with the driving unit, the movable member moves with the plunger as to maintain a position of the plunger relative to the movable member along the displacement axis, and that, by operating the driving unit with the movable member being decoupled from the driving unit, the plunger is displaced while a position of the movable member is maintained.

2. The dosing unit of claim 1, wherein the movable member is rotatable with respect to the stationary member between the charging valve position and the discharging valve position, wherein an axis of rotation of the movable member is the displacement axis.

3. The dosing unit of claim 1, wherein operating the driving unit in a charging driving direction results in the movable member moving into the charging valve position, followed by displacing the plunger in a distal direction, and in that operating the driving unit in a discharging driving direction opposite to the charging driving direction results in the movable member moving into the discharging valve position, followed by displacing the plunger in a proximal direction.

4. The dosing unit of claim 1, wherein operating the driving unit in a charging driving direction results in displacing the plunger into the distal plunger end position, followed by moving the movable member in a discharging valve direction, and in that operating the driving unit in a discharging driving direction opposite to the charging driving direction results in displacing the plunger into the distal plunger end position, followed by moving the movable member in the discharging valve direction.

5. The dosing unit of claim 1, wherein the dosing unit comprises an arrangement of stationary stops and movable stops, wherein the movable member decouples from the driving unit upon a movable stop engaging a corresponding stationary stop and couples to the driving unit upon the movable stop disengaging the corresponding stationary stop.

6. The dosing unit of claim 1, wherein the movable member is adapted to selectively couple to the driving unit by radial and/or axial contact force.

7. The dosing unit of claim 6, wherein radial and/or axial contact force is controlled in dependence of an axial position of the plunger in the metering cavity and/or in dependence of the position of the movable member relative to the stationary member.

8. The dosing unit of claim 7, wherein radial contact force is controlled by controlling a radial dimension of the plunger.

9. The dosing unit of claim 1, wherein the dosing unit comprises a wrap spring clutch, the wrap spring clutch selectively decoupling the movable member from the driving unit when the movable member adopts either of the charging valve position or the discharging valve position.

10. The dosing unit of claim 9, wherein a spring of the wrap spring clutch selectively couples a plunger coupler and the movable member.

11. The dosing unit of claim 9, wherein a proximal spring end of the wrap spring clutch acts as movable charging stop and a distal spring end of the wrap spring clutch acts as movable discharging stop, the movable charging stop being adapted to engage a stationary charging stop when the movable member adopts the charging valve position and the movable discharging stop being adapted to engage a stationary discharging stop when the movable member adopts the discharging valve position, thus decoupling the movable member from the driving unit.

12. The dosing unit of claim 1, wherein coupling and decoupling of the movable member to the driving unit is controlled, at least in part, by controlling a driving direction of the driving unit.

13. The dosing unit of claim 1, wherein the dosing unit comprises or is adapted to couple to a movable member position detector and/or a plunger position detection unit.

14. A fluidic assembly, comprising:
- a dosing unit of claim 1; and
- a drug reservoir, the drug reservoir being in fluidic connection with an inlet valve of the dosing unit.

15. An ambulatory infusion device for infusion of a liquid drug into a user's body over an extended time period, comprising:
- a reversible driving unit;
- a drug reservoir, the drug reservoir being adapted to comprise the liquid drug;
- a dosing unit according to claim 1, the charging valve of the dosing unit being in fluidic connection with the drug reservoir, the dosing unit being coupled to the driving unit;
- an outlet assembly in fluidic connection with the discharging valve of the dosing unit; and
- a controller unit adapted to control the driving unit for drug infusion over the extended time period.

16. The dosing unit of claim 1, wherein the plunger selectively couples the movable member to the driving unit.

* * * * *

UNITED STATES PATENT AND TRADEMARK OFFICE
CERTIFICATE OF CORRECTION

PATENT NO. : 8,500,700 B2  
APPLICATION NO. : 13/046022  
DATED : August 6, 2013  
INVENTOR(S) : Haueter et al.

Page 1 of 1

It is certified that error appears in the above-identified patent and that said Letters Patent is hereby corrected as shown below:

In the Specifications

Col. 3, Line 18, "the present disclosure is direct towards" should read --the present disclosure is directed towards--;

Col. 5, Line 33, "according the present" should read --according to the present--;

Col. 13, Lines 19-20, "designed as integral unit" should read --designed as an integral unit--;

Col. 14, Line 13, "may included in" should read --may be included in--;

Col. 14, Line 48, "for a person ordinary skilled" should read --for a person of ordinary skill--;

Col. 17, Line 30, "the dosing unit 1 acts is a" should read --the dosing unit 1 acts as a--;

Col. 20, Line 15, "legs 362a, 362" should read --legs 362a, 362b--;

Col. 21, Line 23, "receives it electrical" should read --receives its electrical--; and Col. 21, Line 29, "1,2,3" should read --1, 2, 3--.

Signed and Sealed this  
Fourth Day of February, 2014

Michelle K. Lee  
*Deputy Director of the United States Patent and Trademark Office*